US012808880B2

(12) United States Patent
Jacobsen et al.

(10) Patent No.: US 12,808,880 B2
(45) Date of Patent: Nov. 24, 2026

(54) HYPERPHOSPHORYLATED TAU IN HUMAN CEREBROSPINAL FLUID BY LC-MS

(71) Applicant: H. LUNDBECK A/S, Valby (DK)

(72) Inventors: Anne-Marie Jacobsen, Valby (DK); Line Rorbaek Olsen, Valby (DK); Frank Schalk, Assen (NL); Nico van de Merbel, Assen (NL)

(73) Assignee: H. LUNDBECK A/S, Valby (DK)

( * ) Notice: Subject to any disclaimer, the term of this patent is extended or adjusted under 35 U.S.C. 154(b) by 457 days.

(21) Appl. No.: 18/579,620

(22) PCT Filed: Aug. 4, 2022

(86) PCT No.: PCT/EP2022/071958
§ 371 (c)(1),
(2) Date: Jan. 16, 2024

(87) PCT Pub. No.: WO2023/012278
PCT Pub. Date: Feb. 9, 2023

(65) Prior Publication Data
US 2024/0319203 A1 Sep. 26, 2024

(30) Foreign Application Priority Data
Aug. 6, 2021 (EP) .................................... 21190078

(51) Int. Cl.
*G01N 33/68* (2006.01)

(52) U.S. Cl.
CPC ..... *G01N 33/6848* (2013.01); *G01N 33/6842* (2013.01); *G01N 33/6896* (2013.01); *G01N 2800/2821* (2013.01); *G01N 2800/52* (2013.01)

(58) Field of Classification Search
CPC ....... G01N 2800/2821; G01N 2800/52; G01N 33/6842; G01N 33/6848; G01N 33/6896
See application file for complete search history.

(56) References Cited

U.S. PATENT DOCUMENTS

| | | | |
|---|---|---|---|
| 2017/0029960 A1 | 2/2017 | Benitez Aguilar et al. | |
| 2018/0016330 A1* | 1/2018 | Pedersen | A61P 25/00 |
| 2019/0234966 A1* | 8/2019 | Steen | G01N 33/6896 |

FOREIGN PATENT DOCUMENTS

| | | | |
|---|---|---|---|
| WO | 2019/213612 | 11/2019 | |
| WO | 2020/193500 | 10/2020 | |
| WO | WO-2021030615 A1 * | 2/2021 | A61P 25/28 |

OTHER PUBLICATIONS

Previs, Michael J., et al. "Quantification of protein phosphorylation by liquid chromatography-mass spectrometry." Analytical chemistry 80.15 (2008): 5864-5872.

(Continued)

*Primary Examiner* — Jennifer Wecker
(74) *Attorney, Agent, or Firm* — Robin L. Teskin; Baker, Donelson, Bearman, Caldwell & Berkowitz, PC

(57) ABSTRACT

The present invention relates to a method of measuring pS396 Tau in a sample comprising the steps of i-iv, i) Treating a CSF sample from a subject suffering or suspected to be suffering from a Tau pathology with trypsin, ii) Subjecting the sample in step i) to a dephosphorylation agent and subsequently take part of the sample aside for step iv) before proceeding to step iii) with the remaining sample, iii) Subjecting the dephosphorylated sample from step ii) to a second trypsin treatment, iv) Measuring the amount of the Tau peptides (SPVVSGDTSPR) corresponding to Tau residues 396-406 in the samples from step ii) and step iii) using LC-MS.

12 Claims, 9 Drawing Sheets

Specification includes a Sequence Listing.

(56) References Cited

OTHER PUBLICATIONS

Taniguchi-Watanabe S, Arai T, Kametani F, Nonaka T, Masuda-Suzukake M, Tarutani A, Murayama S, Saito Y, Arima K, Yoshida M, Akiyama H. Biochemical classification of tauopathies by immunoblot, protein sequence and mass spectrometric analyses of sarkosyl-insoluble and trypsin-resistant tau. Acta neuropathologica. Feb. 2016;131:267-80.

Barthélemy NR, Mallipeddi N, Moiseyev P, Sato C, Bateman RJ. Tau phosphorylation rates measured by mass spectrometry differ in the intracellular brain vs. extracellular cerebrospinal fluid compartments and are differentially affected by Alzheimer's disease. Frontiers in aging neuroscience. May 21, 2019;11:121.

Russell CL, Mitra V, Hansson K, Blennow K, Gobom J, Zetterberg H, Hiltunen M, Ward M, Pike I. Comprehensive quantitative profiling of tau and phosphorylated tau peptides in cerebrospinal fluid by mass spectrometry provides new biomarker candidates. Journal of Alzheimer's disease. Jan. 1, 2017;55(1):303-13.

* cited by examiner

A. Analysis of SPVVSGDTSPR after workflow 1 (WF1)

| Analyte | MRM transition (Da) | Retention time (min) | Peak Height (cps) | Peak Area (counts) |
|---|---|---|---|---|
| Tau(396-406) WF1 SPVVSGDTSPR | 558.3>729.3 | 8.044 | 3204 | 30489 |

B. Analysis of SPVVSGDTSPR

| Analyte | MRM-transition (Da) | Retention time (min) | Peak Height (cps) | Peak Area (counts) |
|---|---|---|---|---|
| Tau(396-406) WF2 SPVVSGDTSPR | 558.3>729.3 | 8.049 | 5226 | 52585 |

HYPERPHOSPHORYLATED TAU IN HUMAN CEREBROSPINAL FLUID BY LC-MS

This application is a U.S. National Phase Appl. submitted under 35 U.S.C. 371 based on International Appl. No. PCT/EP2022/071958, filed Aug. 4, 2022, which claims priority to European Appl. No. 21190078.2, filed Aug. 6, 2021, each and all of which are hereby incorporated by reference in their entirety.

SEQUENCE LISTING DISCLOSURE

This application includes as part of its disclosure an electronic sequence listing text file named "11432570016001.xml", having a size of 5,183 bytes and created on Jan. 12, 2024, which is hereby incorporated by reference in its entirety.

FIELD OF THE INVENTION

The present invention relates to a method to determine hyperphosphorylated Tau, and in particular Tau phosphorylated on the Serine residue in position 396 (S396) of Tau, in human cerebrospinal Fluid (CSF) using a trypsin digestion and a Liquid Chromatography/Mass Spectrometry workflow (LC-MS).

BACKGROUND OF THE INVENTION

A method to follow progression of Tau pathology in Tau pathologies such as Alzheimer's disease (AD) or Down's syndrome can be of great relevance in order to diagnose patients or monitor their disease stage. Currently there is great clinical need for diagnostic and predictive biomarkers, as well as biomarkers for classification purposes, to identify patients in the early stages of Tau pathology, such as seen for patients with mild cognitive impairment (MCI) who may later progress to AD.

Promising cerebrospinal fluid (CSF) biomarker candidates are total Tau protein and phosphorylated Tau protein (pTau) which may prove to have sufficient diagnostic accuracy and predictive power. The present inventors have developed an assay that is able to detect hyperphosphorylated Tau using Tau protein phosphorylated at serine 396 (pS396) and has shown that this analysis/biomarker can show effect of e.g. antibody treatment in transgenic mouse expressing high levels of human Tau and Taupatology.

The inventors of the present invention have found a reliable method of measuring pS396-Tau using a method that takes advantage of the fact that trypsin does not cleave after amino acid Lysine 395 when Tau is phosphorylated at Serine 396 (pS396), which is a hall mark in hyperphosphorylated Tau phathology. Hence only a Tau protein which is not phosphorylated at this site will be cleaved by Trypsin and will yield the peptide SPVVSGDTSPR (SEQ ID NO: 1), where S is the unphosphorylated S396 serine.

The Tau protein is a highly complex structure consisting of (at least) 6 proteoforms (ranging from 352 to 441 amino acids and containing more than 80 possible sites for post-translational modifications (PTMs). The heterogenous structure is a challenge for mass spectrometric analysis of the protein, since the mass of the signature peptide of interest may vary depending on possible PTMs.

In this invention, the signature peptide of interest contains Serine 396. The cleavage points of Trypsin are the carbonyl (C) side of the amino acids Lys (K) and Arg (R), except if the following amino acid is phosphorylated. Hence, for analysis of pS396-Tau, tryptic cleavage yields the signature peptide TDHGAEIVYK[p]SPVVSGDTSPR (SEQ ID NO: 2). However, this peptide may (or may not) be phosphorylated on the amino acids T386, Y394, S400, T403 and S404. The various possible combinations of these phosphorylations result in hundreds of different peptides, which will each have a specific chromatographic retention time and/or molecular mass for LC-MS analysis. If direct quantitative analysis of the signature peptide containing pS396 were to be performed using LC-MS, it would require quantification of each individual variation of phosphorylated peptide. This approach would require extensive analytical work, and more important, the analytical signal for pS396 would be "diluted" into these various peptides. Since the expected concentrations of pS396 in human CSF are in the low pM range, the requirements for sensitivity of the mass spectrometer will likely be a limitation if applying such a direct analysis.

Therefore, an aspect of the invention lies in the tryptic digestion of the sample obtained from CSF. In this invention an indirect analytical approach is applied that allows the analysis to be focused on a single human Tau derived peptide SPVVSGDTSPR [aa 396-406] (SEQ ID NO: 1).

The method takes advantage of the fact that phosphorylation on S396 prevents trypsin from cleaving the protein chain at this position, and tryptic digestion of S396-phosphorylated Tau protein will therefore yield the peptide TDHGAEIVYK[p]SPVVSGDTSPR (SEQ ID NO: 2). Hence only Tau protein not phosphorylated at S396 will be cleaved by Trypsin in the first workflow and yield the peptide SPVVSGDTSPR (SEQ ID NO: 1) (after removing all possible phosphorylations with phosphatase treatment). Hence the workflow 1 analysis of SPVVSGDTSPR corresponds to the amount of unphosphorylated S396.

In workflow 2 a second tryptic digest is applied. The peptide SPVVSGDTSPR (SEQ ID NO: 1) will be unaffected of this treatment, whereas TDHGAEIVYKSPVVSGDTSPR will now be cleaved between amino acids Lysine 395 and Serine 396 since the peptide is no longer phosphorylated at Serine 396 (removed by the phosphatase treatment). Hence the second tryptic digest yields additional amounts of SPVVSGDTSPR and the workflow 2 analysis corresponds to the sum of unphosphorylated S396 and phosphorylated S396 (equivalent to total amount of Tau).

The difference of the amount of SPVVSGDTSPR [396-406] (SEQ ID NO: 1) measured in workflow 1 and workflow 2 hence equals the amount of Tau protein originally phosphorylated at S396 (pS396-Tau).

SUMMARY OF THE INVENTION

The present invention relates to a method of measuring pS396 Tau in a CSF sample comprising the steps of i) Treating a (in vitro) CSF sample from a subject suffering or suspected to be suffering from a Tau pathology with trypsin, ii) Subjecting the sample in step i) to a dephosphorylation agent and subsequently taking part of the sample aside for step iv) before proceeding to step iii) with the remaining sample, iii) Subjecting the dephosphorylated sample from step ii) to a second trypsin treatment, iv) Measuring the amount of the Tau peptides (SPVVSGDTSPR (SEQ ID NO: 1)) corresponding to Tau residues 396-406 in the samples from step ii) and step iii) using LC-MS.

The method can be used in diagnosing a patient with a Tau pathology or monitoring the disease of a patient with a Tau pathology. Alternatively, it's believed that the method can be used to monitor the treatment effect of patients with a Tau pathology.

Top panes (A+B) show the analytical peaks after first tryptic digest and dephosphorylation: A: The analytical peak for TDHGAEIVYKSPVVSGDTSPR correspond to Tau phosphorylated on S396 (miscleavage) whereas B: SPVVSGDTSPR correspond to Tau not phosphorylated on S396.

The bottom panes (C+D) show analytical peaks obtained after second tryptic digest: C: TDHGAEIVYKSPVVSGDTSPR is not detectable as this is now cleaved at the Lysine 395 site (S396 is no longer phosphorylated). D: The analytical peak for SPVVSGDTSPR increases with an area corresponding the peak in pane A. This additional area corresponds to the amount of Tau phosphorylated at S396 (pS396).

Figure 1:
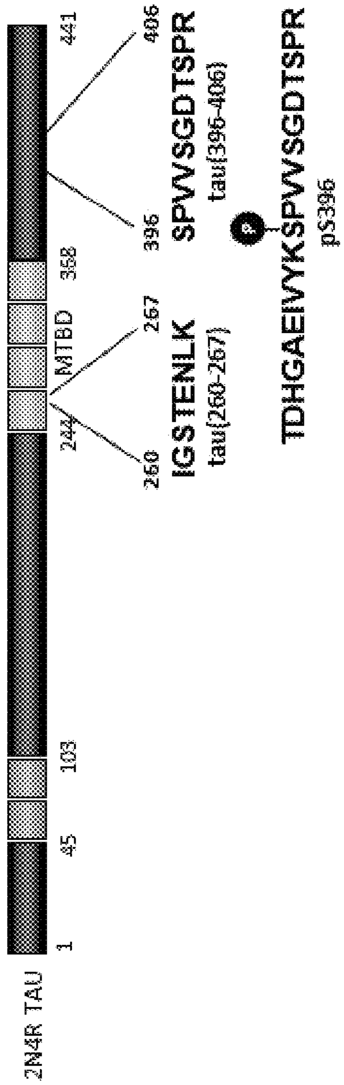
FIG. 1. Schematic diagram of the full-length Tau protein and the selected peptides, Tau(260-267) and Tau(396-406) for LC-MS analysis. The figure also indicates the position of phosphorylation on S396 (pS396) and the peptide TDHGAEIVYK[p]SPVVSGDTSPR (Tau(386-406)), which is the result of miscleavage at Lysine 395. pS396-Tau is indirectly measured as the difference in Tau peptide (amino acids 396-406) concentration before and after dephosphorylation.
Figure 2:
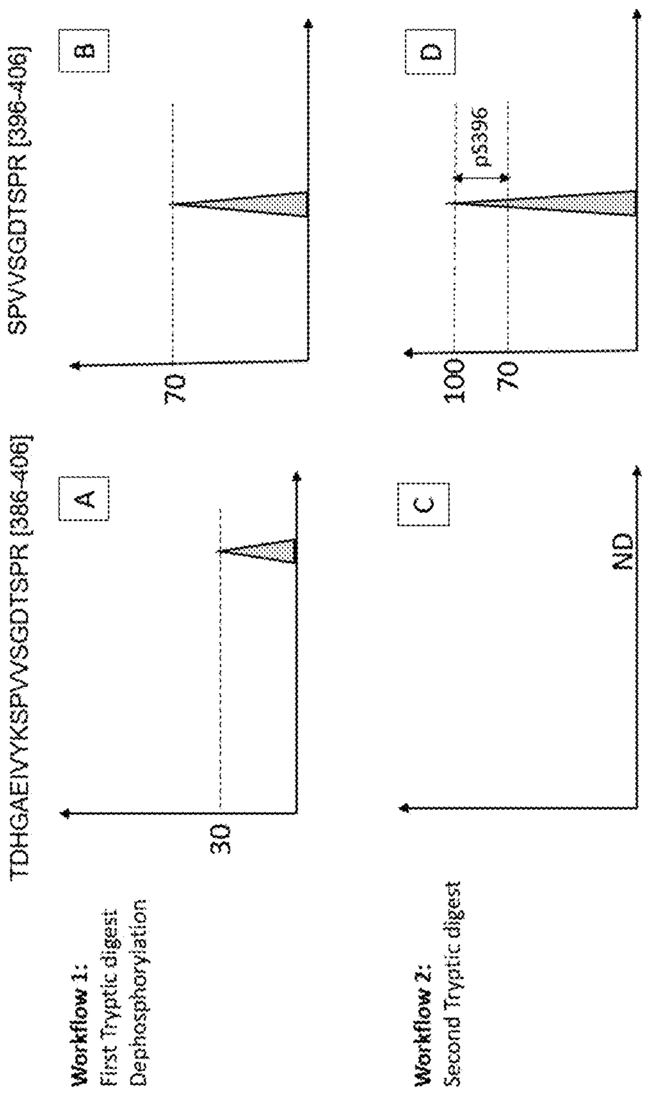
FIG. 2. Theoretical LC-MS/MS chromatograms showing the signature peptides obtained in the individual steps of the sample workflow for analysis of S396 phosphorylated Tau, exemplified by 30% phosphorylation on S396. SPVVSGDTSPR (SEQ ID NO: 1) is measured in the method, whereas TDHGAEIVYKSPVVSGDTSPR (SEQ ID NO: 2) is only included in this figure for reference.
Figure 3A:
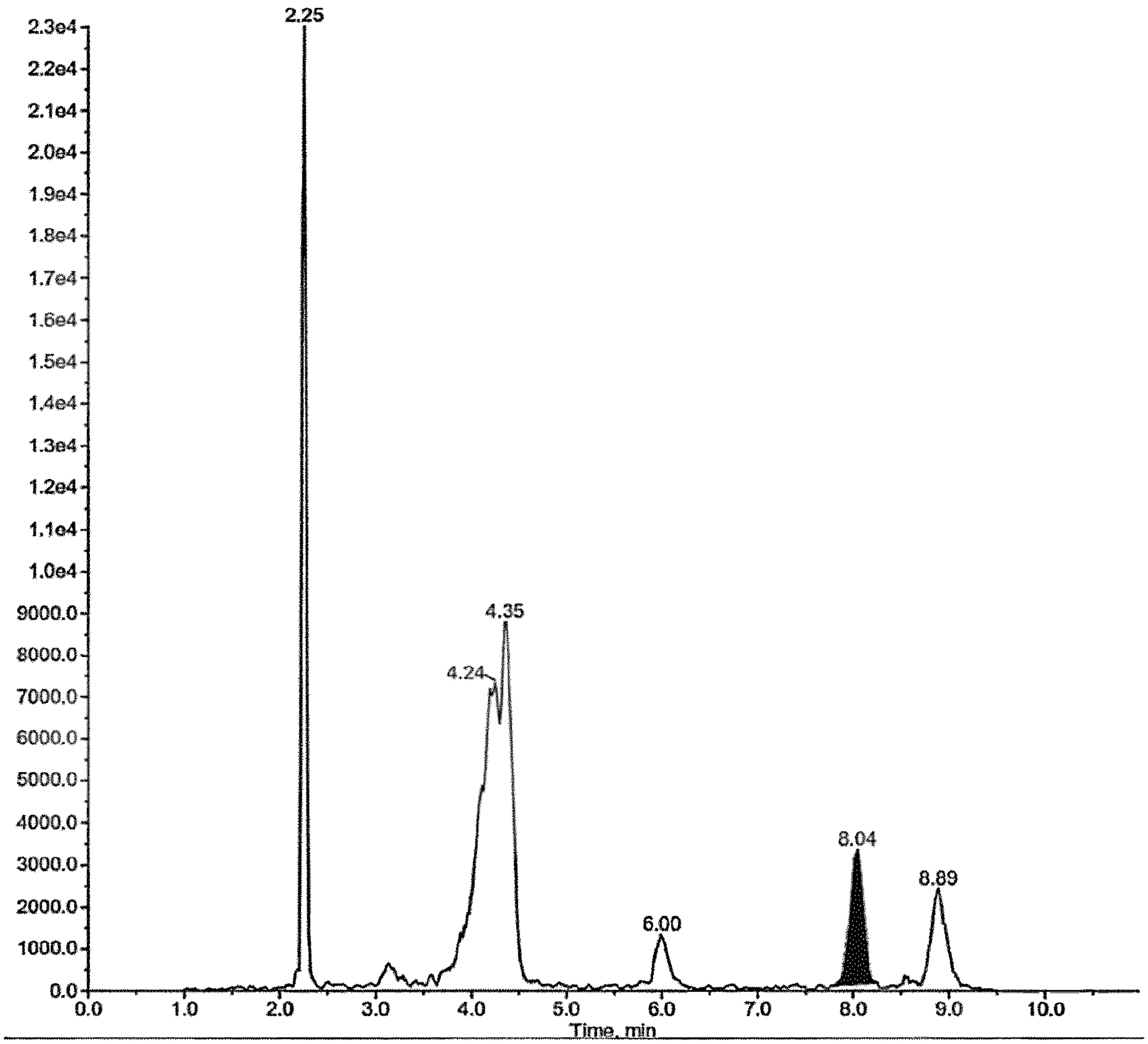
Figure 3B:
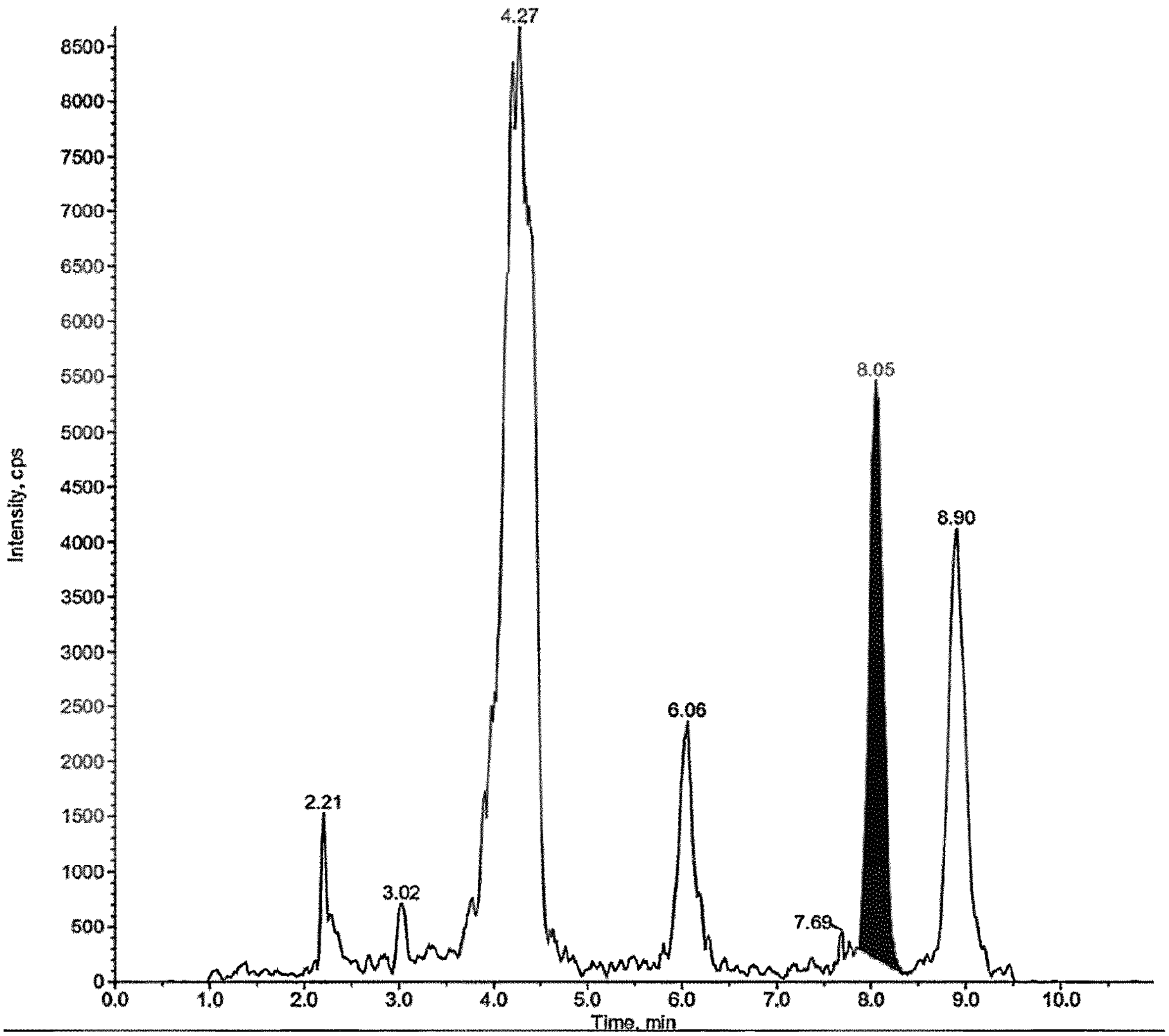
Figure 4A:
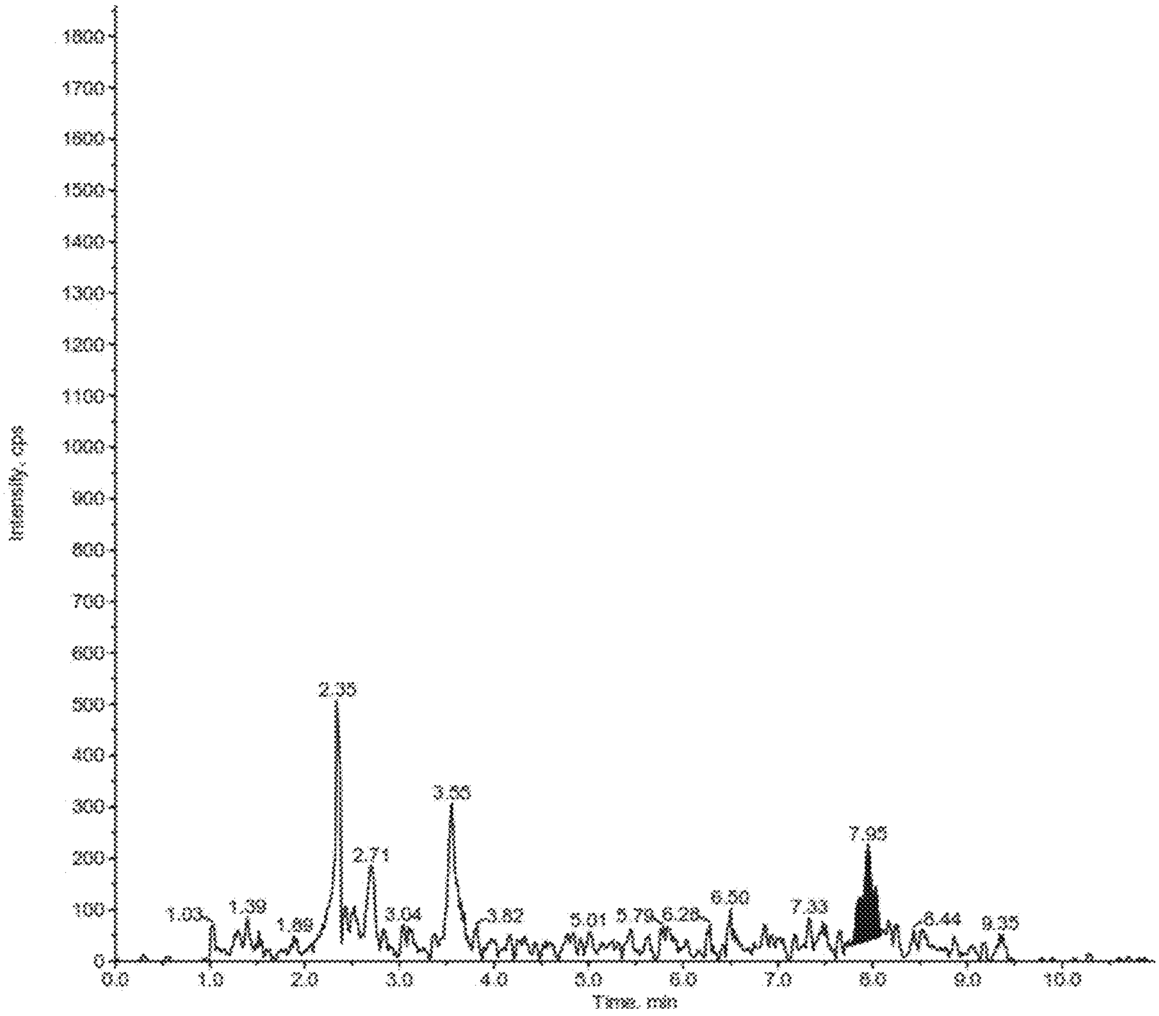
Figure 4B:
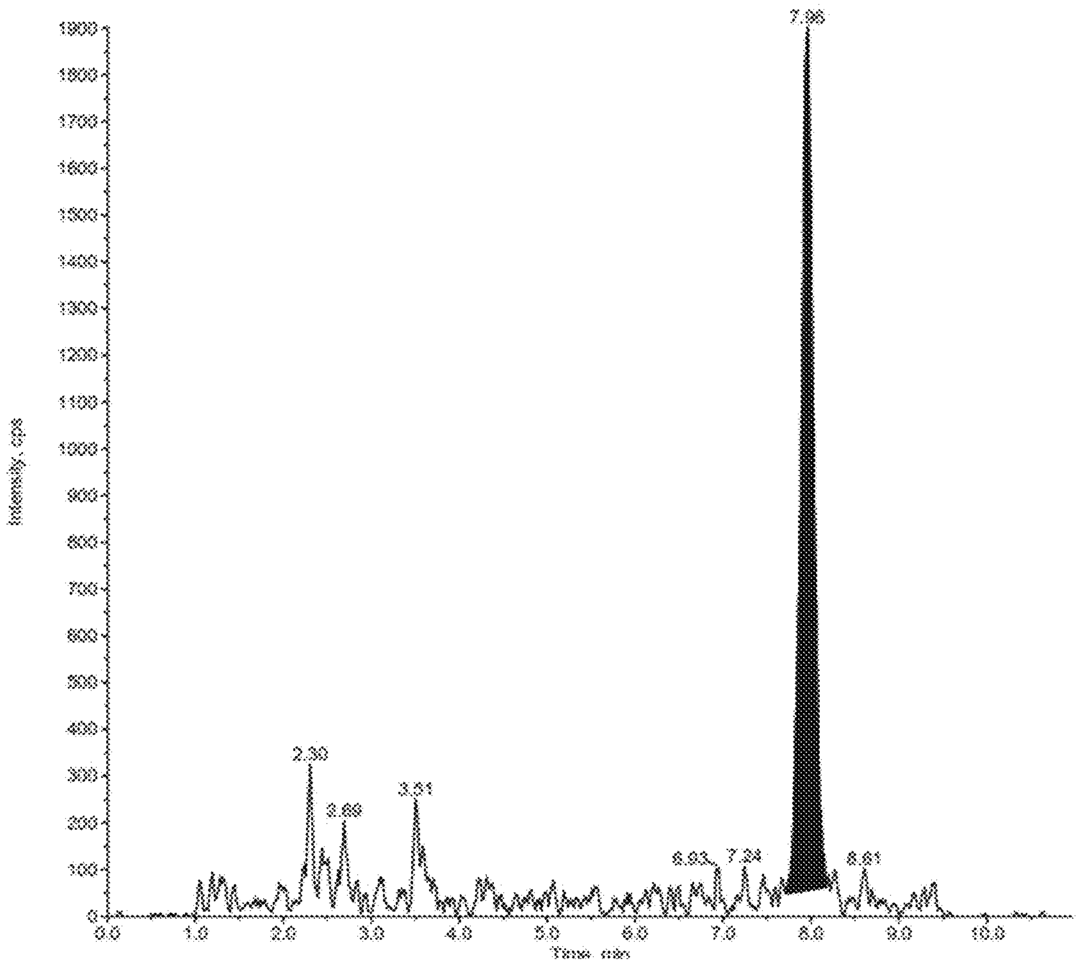
Figure 4C:
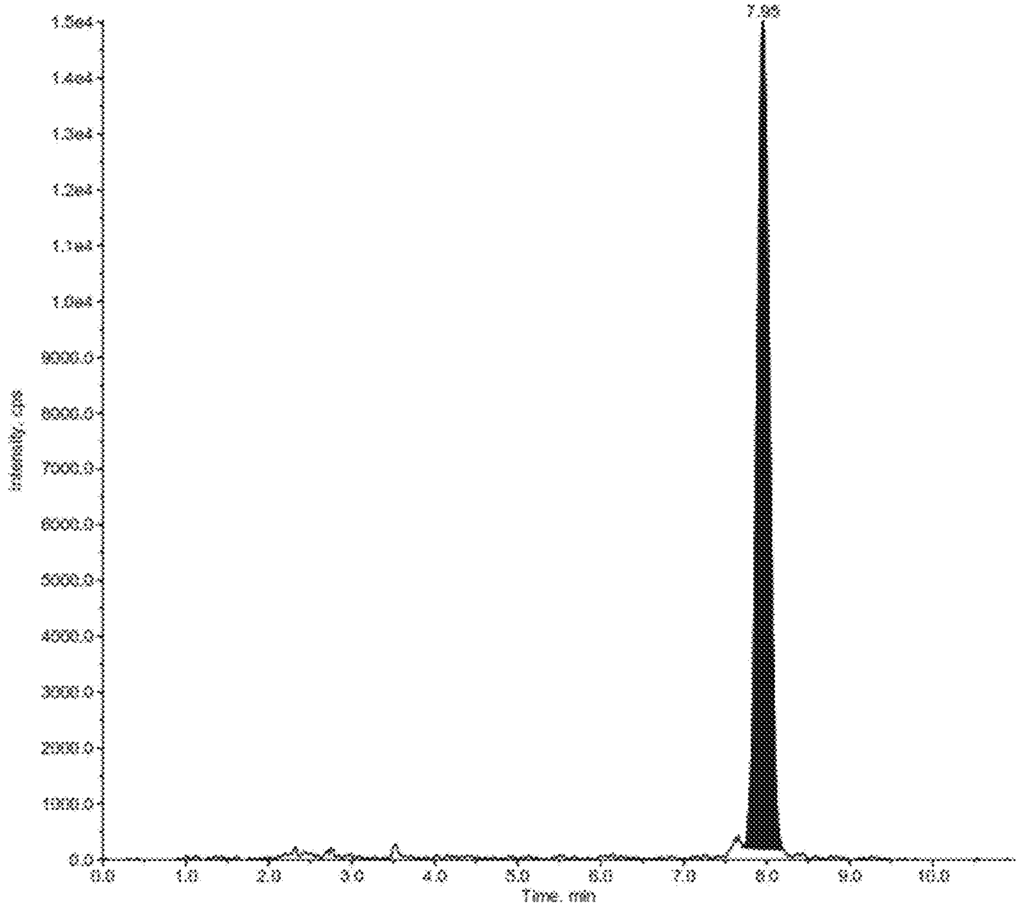
Figure 4D:
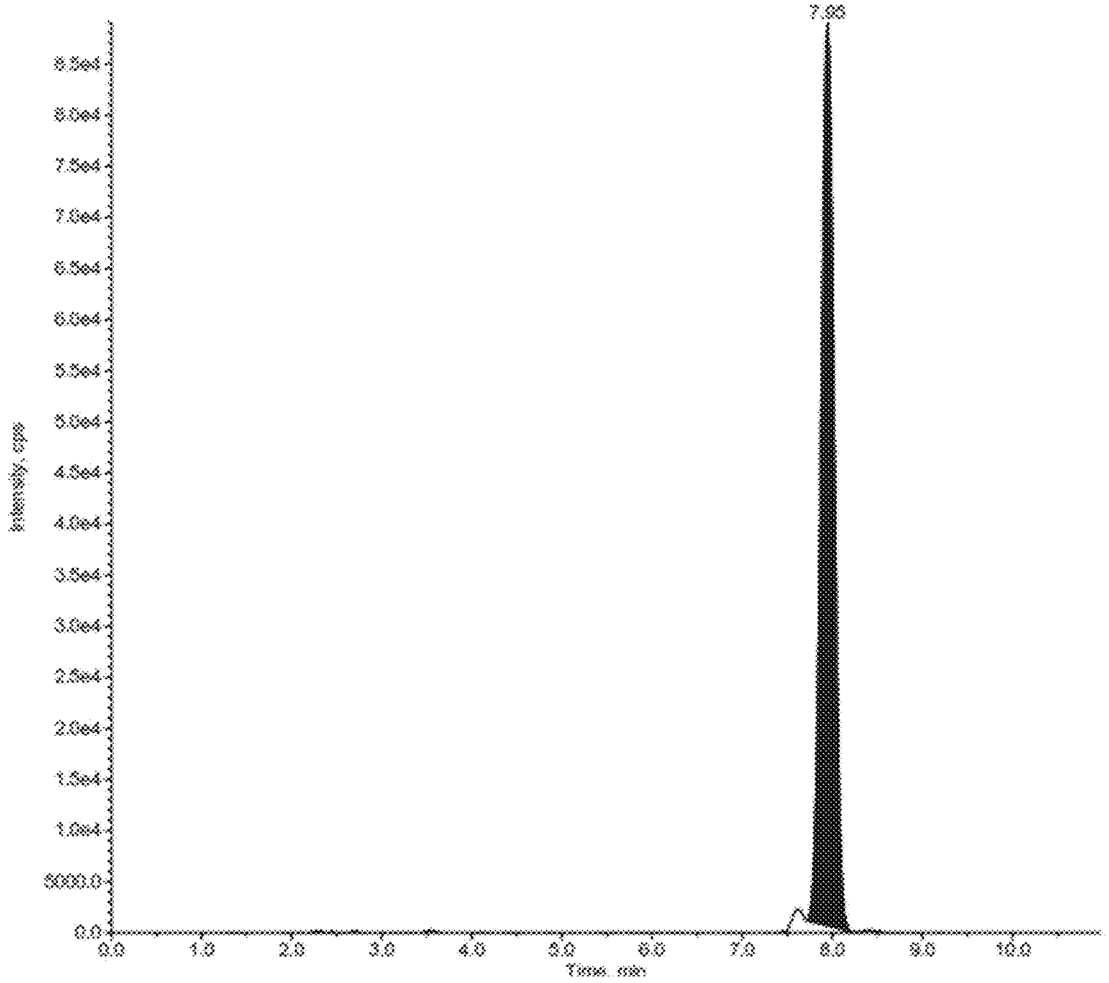

FIG. 3A-B. LC-MS/MS chromatograms for analysis of endogenous levels of Tau(396-406) SPVVSGDTSPR peptide in human CSF. Panel A show the chromatogram obtained after workflow 1 (i.e. after first tryptic digest and de phosphorylation) and Panel B show the chromatogram after workflow 2 (i.e. after second tryptic digest). Note that the analytical peak area increases from 30489 counts in WF1 to 52585 counts in WF2, equivalent to a difference of 22096 counts or 42%. This difference corresponds to the amount of phosphorylation on S396 (pS396).

FIG. 4A-D. LC-MS/MS chromatograms for analysis of Tau(396-406) SPVVSGDTSPR peptide in calibration standards prepared in artificial CSF. Panel 1 shows a blank sample, Panel 2 show a 2 pM calibration standard corresponding to the lower limit of quantification (LLOQ), Panel 3 show a 20 pM calibration standard (typical level in human CSF) and Panel 4 show a 100 pM calibration standard corresponding to upper level of quantification (ULOQ). In each panel, the Figure a is the non-labelled peptide and Figure b is the internal standard (15N-SPVVSGDTSPR).

Figure 5:
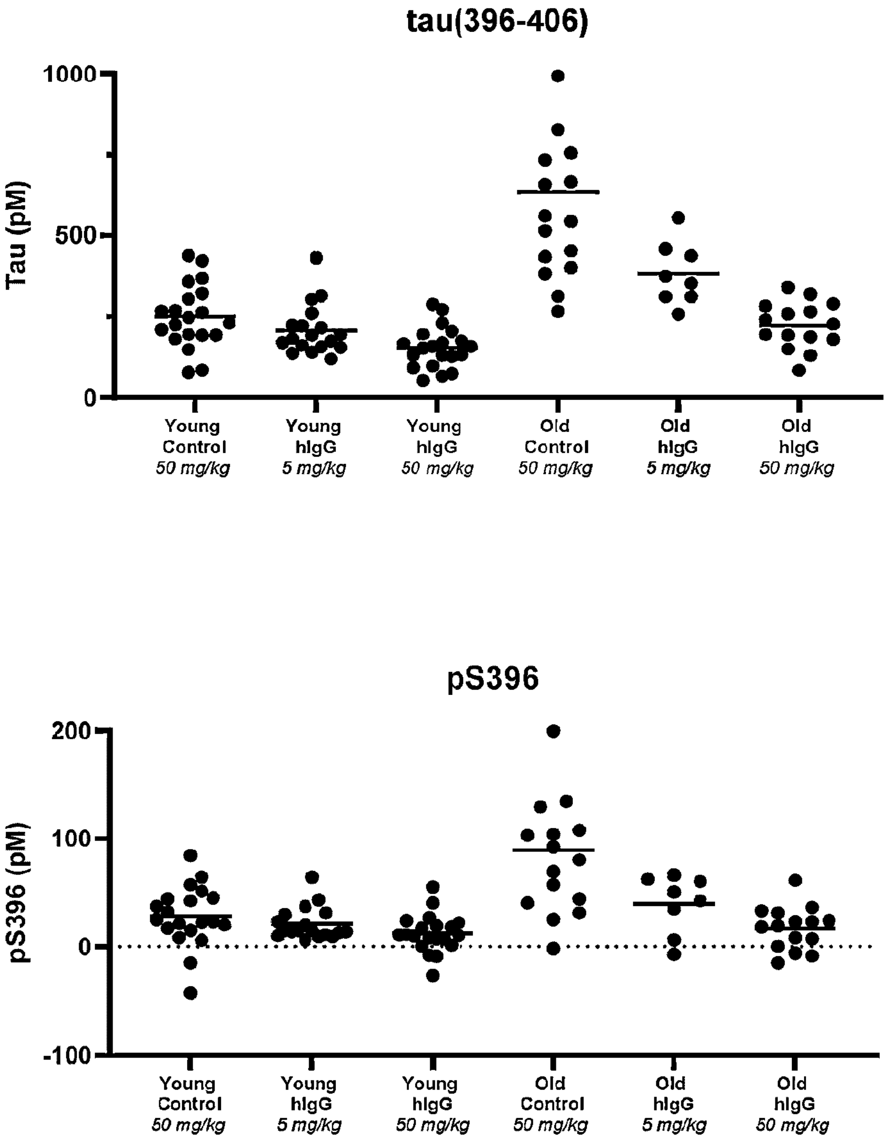

FIG. 5. Data obtained for analysis of CSF samples from transgenic mice (rtg4510) after 6 weeks administration (once weekly) of either a control hIgG antibody (B12, not expected to bind to Tau) or a monoclonal hIgG anti-Tau antibody developed to target the pS396-Tau epitope. Young mice were 3.5 months when CSF were sampled and are known to have low levels of Tau pathology. Old mice were 9 months when CSF were sampled and are known to have severe levels of Tau pathology at that age. Top pane show results for analysis of Tau(396-406) and the bottom pane show results for S396 phosphorylated Tau calculated as the difference between Tau(396-406) before and after the second tryptic digest.

In the control antibody treated mice, it can be observed that the measured concentrations of tau(396-406) and pS396 is higher in the old compared to young mice. Furthermore, in the old mice (with Tau pathology) a dose dependent reduction of tau(396-406) and pS396 is observed after treatment with anti-Tau hIgG.

SEQUENCES INCORPORATED BY REFERENCE

SEQ ID NO:1 SPVVSGDTSPR (Tau 396-406)
SEQ ID NO: 2 TDHGAEIVYKSPVVSGDTSPR (Tau 386-406)
SEQ ID NO: 3 IGSTENLK (Tau 260-267)

DESCRIPTION OF THE INVENTION

The present invention relates to an assay measuring the amount of Tau phosphorylated at the Serine residue S396 (pS396) in a human cerebrospinal fluid (CSF) sample. The aim is to get a measure of hyperphosphorylated Tau in the CSF of subjects by measuring pS396, particular in subjects where a diagnosis is desired or where the effect of a treatment is to be determined or monitored. These subjects are suffering or suspected to be suffering from a Tau pathology such as Alzheimer's disease (AD) and Down's Syndrome.

The inventors of the present invention have used analysis of pS396 Tau as an indirect measure of hyperphosphorylated Tau in CSF. By using a tryptic cleavage step, the inventors of the present invention have taken the advantage of trypsins inability to cleave Tau just before the Serine residue 396 (S396) in Tau when phosphorylated.

An aspect of the invention therefore lies in the tryptic digestion of the sample obtained from CSF. If Tau is unphosphorylated at the position S396 trypsin can cleave just before residue S396 and generate a peptide SPVVSGDTSPR [amino acids 396-406]. This fragment is dominant in e.g. healthy subjects without Tau pathology. During the disease stages of a Tau pathology (e.g. AD), Tau will become hyperphosphorylated and the residue S396 will also be phosphorylated. Phosphorylation at S396, generating pS396, will block trypsin's ability to cleave, and tryptic digestion will therefore not give the signature peptide SPVVSGDTSPR. Instead, it will yield a larger peptide TDHGAEIVYKSPVVSGDTSPR.

In one aspect, the invention relates to a method comprising the steps of i) Treating a CSF sample from a subject (e.g. a human) with trypsin,
ii) Subjecting the remaining sample in step i) to a dephosphorylation agent (such as a phosphatase) and subsequently take part of the sample aside for step iv) before proceeding to step iii),
iii) Subjecting the dephosphorylated sample from step ii) to trypsin treatment,
iv) Measuring the amount of the peptides SPVVSGDTSPR in the samples from step ii) and step iii) (e.g. using LC-MS),
v) Optionally, comparing the amount of the Tau peptides (SPVVSGDTSPR) from step ii) and step iii) as measured in step iv)

vi) Optionally, comparing the amount of the Tau peptides (SPVVSGDTSPR) from step ii) and step iii) as measured in step iv) with a control, such as a trypsin digested Tau peptide fragment not affected by phosphorylation (e.g. the Tau peptide comprising the residues 260-267 (IGSTENLK)) (SEQ ID NO: 3).

The measured SPVVSGDTSPR in step ii) above will measure the portion of SPVVSGDTSPR corresponding to unphosphorylated S396 in the CSF sample, because trypsin is only able to cleave between amino acids Lysine 395 and Serine 396 if Serine 396 is unphosphorylated.

In step iii), a second tryptic digest is applied after the dephosphorylation step in step ii). The portion of phoshorylated and uncleaved Tau peptide TDHGAEIVYK-SPVVSGDTSPR from step i) will now be cleaved between amino acids Lysine 395 and Serine 396 since Tau is no longer phosphorylated at Serine 396. Hence the second tryptic digest yields additional amounts of SPVVSGDTSPR corresponding to the sum of unphosphorylated S396 and phosphorylated S396 (total amount of Tau).

Further, the difference of the amount of SPVVSGDTSPR measured directly after step i) (unphosphorylated S396) and the amount of SPVVSGDTSPR measured after the second digestion in step iii) (total Tau) is the amount of Tau protein phosphorylated at S396. IGSTENLK [260-267] serves as a reference peptide since this peptide does not contain any phosphorylation sites, and the same concentrations should be measured before and after the second tryptic digest step. This serves as a confirmatory peptide for measurement of the total concentration of Tau protein.

The trypsin digested peptides in step i) are subjected to a solid phase extraction (SPE) prior to dephoshorylation treatment in order to remove residues of trypsin prior to the dephosphorylation step (to avoid cleavage at S396 when phosphorylation is removed). Prior to dephosphorylation, pH is adjusted to 5.5. At this pH the enzymatic activity of trypsin is minimized whereas the activity of Lambda Protein Phosphatase (λPP) is maintained. In step v) a suitable method for analysis of Tau protein in the above-described assay can be an LC-MS analysis of peptides, Tau(396-406) and Tau(260-267).

The method according to the invention can be used to assess or monitor the Tau pathology of a subject such as a mammal (mouse or monkey) and in particular a human.

The Tau pathology can be seen in many diseases such as Alezheimer's Disease, Down's Syndrome, Argyrophilic Grain Disease (AGD), Psychosis, particularly Psychosis due to AD or Psychosis in patients with AD, apathy due to AD or apathy in patients with AD, psychiatric symptoms of patients with Lewy body dementia, Progressive Supranuclear Palsy (PSP), Frontotemporal dementia (FTD or variants thereof), TBI (traumatic brain injury, acute or chronic), Corticobasal Degeneration (CBD), Picks Disease, Primary age-related Tauopathy (PART), Neurofibrillary tangle-predominant senile dementia, Dementia pugilistica, Chronic traumatic encephalopathy, stroke, stroke recovery, neurodegeneration in relation to Parkinson's disease, Parkinsonism linked to chromosome, Lytico-Bodig disease (Parkinson-dementia complex of Guam), Ganglioglioma and gangliocytoma, Meningioangiomatosis, Postencephalitic parkinsonism, Subacute sclerosing panencephalitis, Huntington's disease, lead encephalopathy, tuberous sclerosis, Hallervorden-Spatz disease and lipofuscinosis. It is envisaged that the method disclosed above, can be used for diagnosing a patient with a Tau pathology, such as Alzheimer's or Down's syndrome. Further, it is believed that the method will also be useful for monitoring the disease of a subject with a Tau pathology.

It is further envisaged that the method disclosed above, can be used for monitoring the treatment effect in a subject with a Tau pathology, such as Alzheimer's or Down's syndrome. In particular, it is believed that the method is useful to monitor any treatments that may be targeting the Tau pathology such as anti-Tau antibody treatment.

EXAMPLES

Example 1: Materials and Reagents

Lambda Protein Phosphatase (λPP, 50 μL of 400 000 units/mL) and 10 mM Manganese(II)chloride (1 mL of 10 mM MnCl2) was obtained from Bioke.

Sep-Pak® tC18 100 mg 96-well SPE plate was obtained from Waters, US. Phosphatase inhibitor cocktail Ill was obtained from Sigma Aldrich.

Trypsin (from porcine pancreas, T0303) was obtained from Sigma Aldrich Trypsin inhibitor was obtained from Sigma Aldrich Biological Samples Human CSF obtained from BioIVT or PrecisionMed Mouse CSF obtained from own laboratory. CSF sampled from rtg4510 mice expressing human ON4R tau harbouring a disease associated mutation P301L.

Preparation of Reagents

| Solution | Preparation |
|---|---|
| Mobile phase A | 0.1% formic acid:0.5% DMSO in water<br>Mix 2.00 mL formic acid and 10 mL DSMO with 2000 mL water |
| Mobile phase B | Methanol |
| Rinse solvent | Acetonitrile:2-propanol:water:formic acid (20:40:40:1, v/v/v/v)<br>Mix 200 mL acetonitrile, 400 mL 2-propanol, 400 mL water and 10.0 mL formic acid |
| Seal wash | 2-propanol:water (10:90, v/v)<br>Mix 100 mL 2-propanol with 900 mL water |
| 0.1% Tween20 in PBS | 0.1% Tween20 in PBS<br>Mix 400 μL Tween20 with 40 mL PBS(10x) and 360 mL water<br>Store at room temperature<br>Expiry date: One week after preparation |
| Artificial CSF (aCSF) | 0.1% Tween20 in PBS + phosphatase inhibitor<br>Mix 1 mL phosphatase inhibitor cocktail III with 50.0 μL Tween20 with 5.00 mL PBS(10×) and 45.0 mL water<br>Store as blank matrix together with the samples −70° C. |
| Digestion solvent | 250 mM ABC in water.<br>Dissolve 4.94 g ammonium bicarbonate in 250 mL water<br>Store at room temperature<br>Expiry date: One week after preparation |
| Dephosphorylation solvent/SPE wash solvent | 100 mM Ammonium acetate pH = 5.5.<br>Dissolve 7.71 g ammonium acetate in 1000 mL water, adjust to pH 5.5 with acetic acid.<br>Store at room temperature<br>Expiry date: One week after preparation |
| 1 mM HCl in water | Mix 83.3 μL HCl (37%) with 1000 mL water.<br>Store at room temperature<br>Expiry date: 3 months after preparation |
| Trypsin solution | 5 mg/mL Trypsin in 1 mM HCl in water<br>Weigh 200 mg trypsin (T0303) and dissolve in 40.0 mL 1 mM HCl in water.<br>If the trypsin weight is more or less than 200 mg, adjust the added volume of 1 mM HCl in water.<br>Aliquot volume: 1.00 mL in 1.5 mL PP cups.<br>Store until use at −20° C.<br>Set the expiration date 1 year after preparation.<br>Aliquots are single use only!!! |

-continued

| Solution | Preparation |
|---|---|
| 1% formic acid in water | 1% formic acid in water<br>Mix 500 μL formic acid with 50 mL water<br>Store at room temperature<br>Expiry date: One week after preparation |

Following Reagents are Prepared Freshly During Sample Preparation. Details of Preparation are Described Under Sample Preparation:

Digestion mix 1 100 μg/mL trypsin in 250 mM ABC in water

Trypsin stop solution 1.00 mg/mL trypsin inhibitor in water

Manganese(II)chloride solution 3.125 mM $MnCl_2$ in water

Lambda protein phosphatase (λPP) solution 36364 units/mL λPP in water

Digestion mix 2 300 μg/mL trypsin in 250 mM ABC in water

Stock Solutions

Stock solution $^{15}$N-Tau protein (1.00 mg/mL) (=21.6 μM, MW=46353.2 g/mol) Dissolve an equivalent of 100 μg in 100 μL 0.1% Tween20 in PBS Stock Solution pS396 Tau Protein (~1.20 mg/mL) (=26.1 μM, MW=45902.2 g/Mol)

This solution is used to demonstrate method suitability and determine the lowest percentage of S396-phosphorylation that reliable can be measured

Example 2: Procedure for Sample Preparation-Workflow 1

First Tryptic Digest

Frozen CSF samples were thawed at room temperature and homogenized by slowly inverting (at least 5 times) and vortexing for 30 seconds. Samples are centrifuged for 1 minute at approximately 500× g and 20° C. and 200 μL sample is pipetted into a 1 mL plate. Add 10.0 μL 0.1% Tween 20 in PBS to the (double) blanks and add 10.0 μL internal standard working solution (2.7 nM $^{15}$N-Tau protein) to all other wells.

Prepare the digestion mix 1 freshly as described under materials and reagents (100 μg/mL trypsin). Mix 100 μL 5 mg/mL trypsin in 1 mM HCl solution with 4900 UL digestion solvent (250 mM ABC in water) in a tube. Add 40.0 μL of the freshly prepared digestion to each well and vortex the plate for 60 minutes at 1200 rpm (thermomixer) and 37° C.

Prepare the digestion stop solution freshly (1.00 mg/mL). Weigh an amount of approximately 1.5 mg trypsin inhibitor and dissolve in the required volume of Milli-Q to achieve a concentration of 1.00 mg/mL.

Add 12.0 μL of the freshly prepared digestion stop solution to each well and vortex the plate for 2 minutes at 1200 rpm (thermomixer or mixmate) and 37° C.

Add 60.0 μL of digestion solvent (250 mM ABC in water) and 300 μL of 0.1% Tween 20 in PBS to each well and vortex-mix.

Solid-Phase Extraction

A solid-phase extraction step is applied to remove residues of trypsin prior the dephosphorylation step (to avoid cleavage at S396 when phosphorylation is removed) and the concentrate the sample.

Condition the SPE-columns (Sep-Pak® tC18 100 mg) with 500 μL methanol followed by condition with 1000 μL Milli-Q water. Load the complete sample onto the SPE-columns. Wash the SPE-columns twice with 1000 μL SPE wash (100 mM ammonium acetate pH=5.5).

Place the SPE plate on a (clean) 500 μL plate and centrifuge the SPE plate on the 500 μL plate for 1 minute at 400*g to collect all the remaining SPE wash (waste). Elute the samples with 450 UL methanol into a new clean 500 μL LoBind plate deep well plate.

Evaporate the solvent to dryness at 65° C. under a gentle stream of nitrogen for approximately 45 minutes and reconstitute the samples with 20.0 L dephosphorylation solvent (100 mM Ammonium acetate pH=5.5). At this pH the enzymatic activity of trypsin is minimized whereas the activity of Lambda Protein Phosphatase (λPP) is maintained.

Dephosphorylation Step

Prepare the $MnCl_2$ 3.125 mM solution by mixing 1000 μL of 10 mM $MnCl_2$ with 2200 UL Milli-Q in a tube. Add 20.0 μL of the (freshly) prepared 3.125 mM $MnCl_2$ solution to the samples. Prepare the λPP solution fresh, by mixing 50.0 μL λPP solution (containing 20 000 units) with 500 μL Milli-Q in the original cup. Add 10.0 μL of the (freshly) prepared λPP solution to the samples and vortex the plate for 120 minutes at 1200 rpm (thermomixer) and 37° C.

Add 50.0 μL dephosphorylation solvent (100 mM Ammonium acetate pH=5.5) to the plate and vortex the plate for 1 minute at 1200 rpm (thermomixer) and 37° C.

Finalize Workflow 1 and Prepare for Workflow 2

Transfer 50.0 μL of the sample to a new 500 μL protein plate. This sample will be used in workflow 2 and undergo a second tryptic digest (workflow 2 plate).

To the original plate, add 50.0 μL 1% formic acid in water and vortex the plate for 1 minute at 1200 rpm and RT. This plate is ready for LC-MS/MS analysis.

Second Tryptic Digest

Prepare the digestion mix 2 freshly (300 μg/mL trypsin) by mixing 300 μL 5 mg/mL trypsin in 1 mM HCl solution with 4700 μL 250 mM ABC solution in a tube. Add 30.0 μL of the freshly prepared digestion mix 2 to each well of the workflow 2 plate and vortex for 60 minutes at 1200 rpm (thermomixer) and 37° C.

Stop the digestion by adding 20.0 μL 1% formic acid in water to the workflow 2 plate and vortex the plate for 1 minute at 1200 rpm and 37° C. This plate is now ready for LC-MS/MS analysis.

Example 3: LC-MS/MS Analysis

Separation from interfering endogenous compounds is achieved by LC-MS/MS using an Acquity HSS T3 (100×2.1 mm, 1.8 μm) analytical column, set at 30° C., and 0.1% formic acid and 0.5% DMSO in water as mobile phase A and methanol as mobile phase B. An 11-minute gradient at a flow rate of 0.500 mL/min is applied running at 5% mobile phase B for the first 1 minute, linearly increasing to 14% B after 9 min, followed by a step to 90% B which is maintained for 1 min before decreasing back to 5% B. Injection volume is 40 μL.

The expected retention time for SPVVSGDTSPR [396-406] is 7.2 min and for IGSTENLK [260-267] it is 6.5 min.

A SCIEX triple quad 6500 mass spectrometer equipped with a turbo ion spray source is used for detection in positive ion mode. The turbo ionspray source is operated in the positive ion mode at an ion spray voltage of 5500V and at a temperature of 500° C. Curtain gas is set at 30.

Quantification is based on multiple reaction monitoring (MRM) using the transitions specified in Table below. A linear (Analyst) calibration curve with a 1/×2 weighting factor is used ranging from 2 to 100 pM Total Tau protein in CSF.

| | Mass dependent parameters | | | | | |
|---|---|---|---|---|---|---|
| | Q1 Mass (Da) | Q3 Mass (Da) | Time (msec) | DP (V) | CE (V) | CXP (V) |
| IGSTENLK | 431.28 | 748.5 | 75 | 50 | 20 | 20 |
| [260-267] | 431.29 | 748.5 | 75 | 50 | 20 | 20 |
| 5 MRM transitions | 431.30 | 748.5 | 75 | 50 | 20 | 20 |
| are summated | 431.31 | 748.5 | 75 | 50 | 20 | 20 |
| | 431.32 | 748.5 | 75 | 50 | 20 | 20 |

-continued

| | Mass dependent parameters | | | | | |
|---|---|---|---|---|---|---|
| | Q1 Mass (Da) | Q3 Mass (Da) | Time (msec) | DP (V) | CE (V) | CXP (V) |
| $_{15}$N-IGSTENLK [260-267] | 436.30 | 757.5 | 100 | 50 | 20 | 20 |
| SPVVSGDTSPR | 551.28 | 719.30 | 75 | 70 | 27 | 15 |
| [396-406] | 551.29 | 719.30 | 75 | 70 | 27 | 15 |
| 5 MRM transitions | 551.30 | 719.30 | 75 | 70 | 27 | 15 |
| are summated | 551.31 | 719.30 | 75 | 70 | 27 | 15 |
| | 551.32 | 719.30 | 75 | 70 | 27 | 15 |
| $_{15}$N-SPVVSGDTSPR [396-406] | 558.30 | 729.30 | 100 | 70 | 27 | 15 |

```
                         SEQUENCE LISTING

Sequence total quantity: 3
SEQ ID NO: 1           moltype = AA  length = 11
FEATURE                Location/Qualifiers
REGION                 1..11
                       note = Human Tau
source                 1..11
                       mol_type = protein
                       organism = synthetic construct
SEQUENCE: 1
SPVVSGDTSP R                                                   11

SEQ ID NO: 2           moltype = AA  length = 21
FEATURE                Location/Qualifiers
REGION                 1..21
                       note = Human Tau
SITE                   10
                       note = K395 - PHOSPHORYLATIONThe Lysine can be
                        phosphorylated
source                 1..21
                       mol_type = protein
                       organism = synthetic construct
SEQUENCE: 2
TDHGAEIVYK SPVVSGDTSP R                                        21

SEQ ID NO: 3           moltype = AA  length = 8
FEATURE                Location/Qualifiers
REGION                 1..8
                       note = Human Tau
source                 1..8
                       mol_type = protein
                       organism = synthetic construct
SEQUENCE: 3
IGSTENLK                                                       8
```

What is claimed is:

1. A method of measuring an amount of the Tau peptides (SPVVSGDTSPR) corresponding to Tau residues 396-406 in a sample comprising the steps of i-iv, i) treating a cerebrospinal fluid sample from a subject suffering or suspected to be suffering from a Tau pathology with trypsin, ii) subjecting the sample in step i) to a dephosphorylation agent and subsequently take part of the sample aside for step iv) before proceeding to step iii) with the remaining sample, iii) subjecting the dephosphorylated sample from step ii) to a second trypsin treatment, and iv) measuring the amount of the Tau peptides (SPVVSGDTSPR) corresponding to Tau residues 396-406 in the samples from step ii) and step iii) using LC-MS.

2. The method according to claim 1, further comprising a step of comparing the amount of the Tau peptides (SPVVSGDTSPR) from step ii) and step iii) as measured in step iv).

3. The method according to claim 1, further comprising a step of comparing the results obtained in step iv) with a control comprising the Tau residues 260-267 (IGSTENLK).

4. The method according to claim 1, wherein the subject is human.

5. The method according to claim 1, wherein the Tau pathology is selected from Alzheimer's Disease, Down's Syndrome, Argyrophilic Grain Disease (AGD), Psychosis, particularly Psychosis due to Alzheimer's Disease or Psychosis in patients with Alzheimer's Disease, apathy due to Alzheimer's Disease or apathy in patients with Alzheimer's Disease, psychiatric symptoms of patients with Lewy body dementia, Progressive Supranuclear Palsy (PSP), Frontotemporal dementia (FTD or variants thereof), TBI (traumatic brain injury, acute or chronic), Corticobasal Degeneration (CBD), Picks Disease, Primary age-related Tauopathy (PART), Neurofibrillary tangle-predominant senile dementia, Dementia pugilistica, Chronic traumatic encephalopathy, stroke, stroke recovery, neurodegeneration in relation to Parkinson's disease, Parkinsonism linked to chromosome, Lytico-Bodig disease (Parkinson-dementia complex of Guam), Ganglioglioma and gangliocytoma, Meningioangiomatosis, Postencephalitic parkinsonism, Subacute sclerosing panencephalitis, Huntington's disease, lead encephalopathy, tuberous sclerosis, Hallervorden-Spatz disease and lipofuscinosis.

6. The method according to claim 1 wherein the Tau pathology is Alzheimer's Disease or Down's Syndrome.

7. Use of the method according to claim 1 for diagnosing a patient with a Tau pathology.

8. Use of the method according to claim 1 for monitoring the disease of a patient with a Tau pathology.

9. Use of the method according to claim 1 for monitoring a treatment effect in the subject suffering from a Tau pathology.

10. The use according to claim 9, wherein the treatment is an anti-Tau antibody treatment.

11. The use according to claim 7, wherein the Tau pathology is selected from Alzheimer's Disease, Down's Syndrome, Argyrophilic Grain Disease (AGD), Psychosis, particularly Psychosis due to Alzheimer's Disease or Psychosis in patients with Alzheimer's Disease, apathy due to Alzheimer's Disease or apathy in patients with Alzheimer's Disease, psychiatric symptoms of patients with Lewy body dementia, Progressive Supranuclear Palsy (PSP), Frontotemporal dementia (FTD or variants thereof), TBI (traumatic brain injury, acute or chronic), Corticobasal Degeneration (CBD), Picks Disease, Primary age-related Tauopathy (PART), Neurofibrillary tangle-predominant senile dementia, Dementia pugilistica, Chronic traumatic encephalopathy, stroke, stroke recovery, neurodegeneration in relation to Parkinson's disease, Parkinsonism linked to chromosome, Lytico-Bodig disease (Parkinson-dementia complex of Guam), Ganglioglioma and gangliocytoma, Meningioangiomatosis, Postencephalitic parkinsonism, Subacute sclerosing panencephalitis, Huntington's disease, lead encephalopathy, tuberous sclerosis, Hallervorden-Spatz disease and lipofuscinosis.

12. The use according to claim 7 wherein the Tau pathology is Alzheimer's Disease or Down's Syndrome.

* * * * *